(12) United States Patent
Grote et al.

(10) Patent No.: US 8,163,912 B2
(45) Date of Patent: Apr. 24, 2012

(54) BERBERINE COMPOUNDS AND PROCESSES FOR THE PREPARATION OF BERBERINE COMPOUNDS

(75) Inventors: Christopher W. Grote, Webster Groves, MO (US); Frank W. Moser, Arnold, MO (US); John E. Johnson, Maryville, IL (US)

(73) Assignee: Mallinckrodt LLC, Hazelwood, MO (US)

( * ) Notice: Subject to any disclaimer, the term of this patent is extended or adjusted under 35 U.S.C. 154(b) by 445 days.

(21) Appl. No.: 12/586,834

(22) Filed: Sep. 29, 2009

(65) Prior Publication Data

US 2010/0081821 A1     Apr. 1, 2010

Related U.S. Application Data

(60) Provisional application No. 61/194,689, filed on Sep. 30, 2008.

(51) Int. Cl.
*C07D 471/06* (2006.01)
*C07D 471/02* (2006.01)

(52) U.S. Cl. .......................................... 546/71; 546/61

(58) Field of Classification Search ............... 546/71, 546/61
See application file for complete search history.

(56) References Cited

U.S. PATENT DOCUMENTS 6,008,356 A    12/1999   Kim et al.
6,255,317 B1    7/2001   Kim et al.
2008/0262331 A1 10/2008  Gerber et al.

OTHER PUBLICATIONS

Mundy et al., "Name Reactions and Reagents in Organic Synthesis", Second Edition, Copyright 2005, John Wiley and Sons, Inc., pp. 96-97.
Banwell et al., "Trifluoromethanesulfonic Anhydride-4-(N,N-Dimethylamino)pyridine as a Reagent . . . ", Journal of the Chemical Society, Chemical Communications, 1995, 24, pp. 2251-2253.
Nagubandi et al., "Novel Condensing Agents for Bischler-Napieralski Type Cyclodehydration", Heterocycles, 1981, 15(1), pp. 165-177.
Hendrickson et al., "Triphenylphosphine Ditriflate. General Oxygen Activator", Tetrahedron Letters, 1975, 4, pp. 277-280.
Seebach et al., "Diasteroselektive Hydroxyalkylierungen in 1-Stellung von . . . ", Helvetica Chimica Acta, 70, 1987, pp. 1357-1379, XP 002557497.

*Primary Examiner* — Charanjit Aulakh

(57) ABSTRACT

The invention is directed to berberine compounds and processes for the preparation of berberine compounds through an intramolecular Bischler-Napieralski cyclization.

22 Claims, No Drawings

BERBERINE COMPOUNDS AND PROCESSES FOR THE PREPARATION OF BERBERINE COMPOUNDS

CROSS REFERENCE TO RELATED APPLICATIONS

This application claims the benefit of the filing date of U.S. Provisional Application Ser. No. 61/194,689, filed Sep. 30, 2008, entitled "Berberine compounds and processes for the preparation of berberine compounds" which is incorporated herein in their entirety.

FIELD OF THE INVENTION

The present invention generally relates to berberine compounds and processes for the preparation of berberine compounds.

BACKGROUND OF THE INVENTION

Berberine compounds are a series of isoquinoline alkaloids having varied therapeutic uses and importance. Many of these alkaloids may be found extensively in plants. Berberine compounds have been prepared through many synthetic pathways, including the Bischler-Napieralski cyclization. During a Bischler-Napieralski cyclization, an additional saturated ring is formed by intramolecular cyclization through an imidoyl intermediate. In most Bischler-Napieralski cyclization reactions, phosphorus oxychloride or phosphorus pentachloride are used as the cyclization reagents. Bischler-Napieralski Cyclization reactions, however, typically require undesirable reaction conditions (e.g., extremely high reaction temperatures) and produce berberine compounds in relatively low yield. Because of the potential therapeutic value of berberine compounds and derivatives thereof, there is a need for efficient synthesis processes for their preparation.

SUMMARY OF THE INVENTION

The present invention may provide berberine compounds and synthetic processes for the preparation of berberine compounds.

Briefly, therefore, one aspect of the present invention encompasses a compound comprising Formula (II):

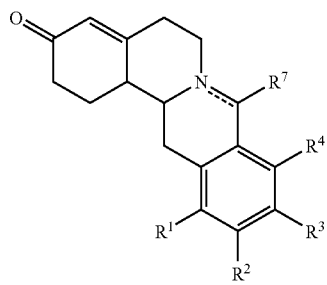

(II)

wherein:
  $R^1$, $R^2$, $R^3$, and $R^4$ are independently selected from the group consisting of cyano, hydroxyl, amino, hydrogen, halogen, hydrocarbyl, substituted hydrocarbyl, and $OR^5$;
  $R^5$ is selected from the group consisting of hydrocarbyl and substituted hydrocarbyl; and
  $R^7$ is selected from the group consisting of hydrogen, hydrocarbyl, and substituted hydrocarbyl.

In an additional aspect, the present invention is also directed to a compound comprising Formula (IIa):

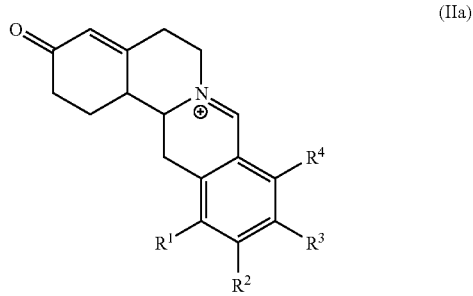

(IIa)

wherein:
  $R^1$, $R^2$, $R^3$, and $R^4$ are independently selected from the group consisting of cyano, hydroxyl, amino, hydrogen, halogen, hydrocarbyl, substituted hydrocarbyl, and $OR^5$; and
  $R^5$ is selected from the group consisting of hydrocarbyl and substituted hydrocarbyl.

In addition to the compounds described above, the present invention also encompasses a process for preparing a compound comprising Formula (II). The process comprises contacting a compound comprising Formula (I) with a proton donor and a proton donor anhydride, the molar ratio of proton donor to proton donor anhydride being from 5:1 to about 1:100, to form a compound comprising Formula (II) according to the following reaction scheme:

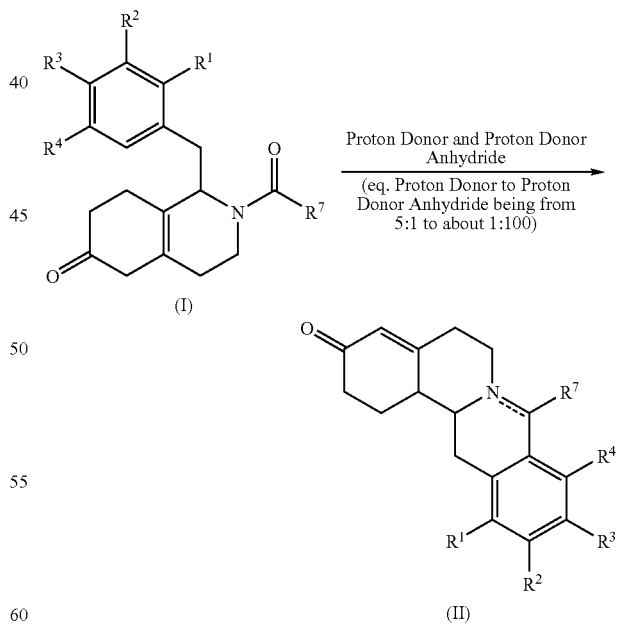

wherein:
  $R^1$, $R^2$, $R^3$, and $R^4$ are independently selected from the group consisting of cyano, hydroxyl, amino, hydrogen, halogen, hydrocarbyl, substituted hydrocarbyl, and $OR^5$;

$R^5$ is selected from the group consisting of hydrocarbyl and substituted hydrocarbyl; and $R^7$ is selected from the group consisting of hydrogen, hydrocarbyl, and substituted hydrocarbyl.

In a further aspect the present invention is directed to a process for preparing a compound comprising Formula (II). The process comprises contacting a compound comprising Formula (I) with a proton donor anhydride, wherein the equivalents of proton donor anhydride to the compound comprising Formula (I) is from about 1.5 to about 1000, to form a compound comprising Formula (II) according to the following reaction scheme:

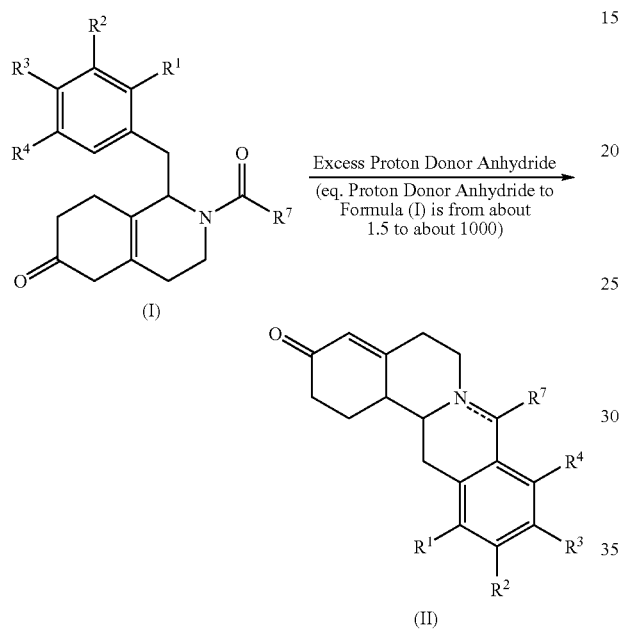

wherein:

$R^1$, $R^2$, $R^3$, and $R^4$ are independently selected from the group consisting of cyano, hydroxyl, amino, hydrogen, halogen, hydrocarbyl, substituted hydrocarbyl, and $OR^5$;

$R^5$ is selected from the group consisting of hydrocarbyl and substituted hydrocarbyl; and $R^7$ is selected from the group consisting of hydrogen, hydrocarbyl, and substituted hydrocarbyl.

Other features and iterations are described in more detail below.

DETAILED DESCRIPTION

The present invention provides newly discovered berberine compounds comprising Formula (II) and processes for preparing the berberine compounds through an intramolecular Bischler-Napieralski cyclization reaction. In particular, it has been discovered that a certain ratio of proton donor to proton donor anhydride or the total amount of proton donor anhydride favors the formation of compounds comprising Formula (II) in the Bischler-Napieralski cyclization reaction. The amount of proton donor anhydride used either alone or in combination with a proton donor is typically an amount that is more than the amount needed to simply consume excess water. The processes of the present invention are particularly surprising and unforeseeable considering that anhydrides were previously limited to use in small amounts as water scavenging agents. Moreover, it was previously thought that even small amounts of anhydride may associate in some manner to the functional groups of the β,γ-bicyclic ketone starting material to kinetically favor the Grewe cyclization by-product.

The berberine compounds of the present invention may be important synthetic intermediates to morphinan compounds that may further be used as analgesics. In one aspect, the berberine compounds of the present invention may be synthetic intermediates to nordihydrothebainone, burprenorphine, codeine, etorphine, hydrocodone, hydromorphone, morphine, nalbuphine, nalbuphone, nalmefene, naloxone, naltrexone, oxycodone, and/or oxymorphone. The berberine compounds of the present invention may also be more stable, more effective, more potent, more reliable, and/or more cost-efficient to produce than other types of berberine compounds. Additionally, the present invention may also provide more efficient and more specific processes for preparing berberine compounds in high yield.

(I) Berberine Compounds

One aspect of the present invention encompasses berberine compounds that may be useful as intermediates in the preparation of morphinan compounds. For purposes of discussion, the compounds of the present invention may comprise Formula (II):

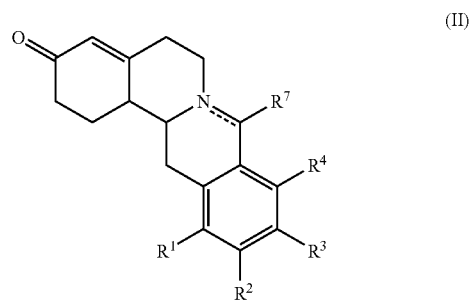

wherein:

$R^1$, $R^2$, $R^3$, and $R^4$ are independently selected from the group consisting of cyano, hydroxyl, amino, hydrogen, halogen, hydrocarbyl, substituted hydrocarbyl, and ORS;

$R^5$ is selected from the group consisting of hydrocarbyl and substituted hydrocarbyl; and $R^7$ is selected from the group consisting of hydrogen, hydrocarbyl, and substituted hydrocarbyl.

The compound comprising Formula (II) may include a number of iterations without departing from the scope of the invention. In one embodiment, the nitrogen atom may be neutral or positively charged (i.e., N$^+$). Generally, when the nitrogen atom is neutral, then — is a single bond. Similarly, when — is a double bond, then the nitrogen atom is N$^+$. $R^1$, $R^2$, $R^3$, and $R^4$ may be independently selected from the group consisting of hydrogen, halogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylether, haloalkoxy, haloalyl, heteroaryl, heterocyclic, hydroxyalkyl, and hydroxyl. The compound comprising Formula II may comprise a counter-ion. In particular, the counter-ion may be selected from the group consisting of chloride, bromide, iodide, trifluoroacetate, trifluoromethanesulfonate, methanesulfonate, acetate, p-toluenesulfonate, sulfate, bisulfate, phosphate, hydrogenphosphate, dihydrogenphosphate, fumarate, malonate, oxalate, formate, tartrate, benzoate, and a combination thereof. In a preferred embodiment, the compound comprising Formula II may comprise a trifluoromethanesulfonate anion.

The present invention is also directed to a compound comprising Formula (IIa):

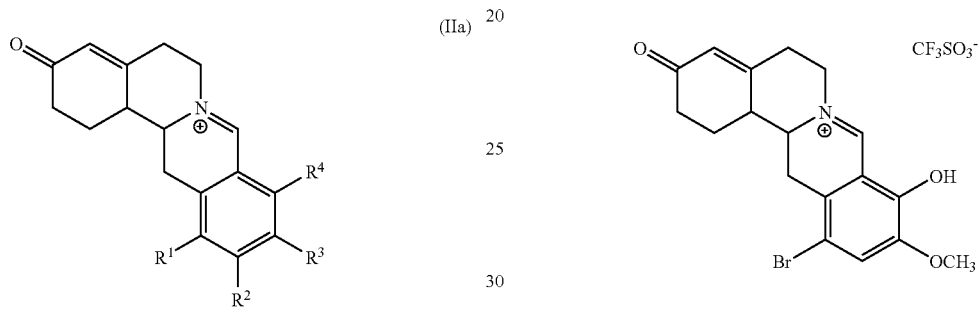

wherein:
  R¹, R², R³, and R⁴ are independently selected from the group consisting of cyano, hydroxyl, amino, hydrogen, halogen, hydrocarbyl, substituted hydrocarbyl, and OR⁵; and
  R⁵ is selected from the group consisting of hydrocarbyl and substituted hydrocarbyl.

The compound comprising Formula (IIa) may also include several iterations. For example, in one embodiment, R¹ is halogen, R² is hydrogen, R³ is OR⁵, R⁴ is hydroxyl, and R⁵ is alkyl or substituted alkyl. In yet another iteration, R¹ is bromide, R² is hydrogen, R³ is OCH³, and R⁴ is hydroxyl. As previously, R¹, R², R³, and R⁴ may be independently selected from the group consisting of hydrogen, halogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylether, haloalkoxy, haloalyl, heteroaryl, heterocyclic, hydroxyalkyl, and hydroxyl. Furthermore, the compound comprising Formula (IIa) may also comprise a counter-ion. A counter-ion may be selected from the group consisting of chloride, bromide, iodide, trifluoroacetate, trifluoromethanesulfonate, methanesulfonate, acetate, p-toluenesulfonate, sulfate, bisulfate, phosphate, hydrogenphosphate, dihydrogenphosphate, fumarate, malonate, oxalate, formate, tartrate, benzoate, and a combination thereof. More specifically, the compound comprising Formula (IIa) may include a trifluoromethanesulfonate anion.

In another embodiment, the present invention is also directed to a compound comprising formula (IIb):

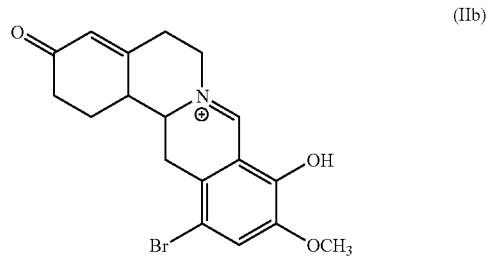

In one alternative of this embodiment, the present invention is directed to a compound comprising the following formula (e.g., a triflate salt):

In the above chemical formula, the compound is $C_{19}H_{19}BrF_3NO_6S$, with an exact mass of 525.01, and a molecular weight of 526.32.

(II) Processes for Preparing Berberine Compounds

The present invention provides an efficient synthetic route for the production of berberine compounds. Among the various aspects of the present invention is a process for preparing berberine compounds and analogs thereof from β,γ-bicyclic ketone compounds (e.g., β,γ-hexahydroisoquinolinones). In particular, the processes for preparing berberine compounds in accordance with the present invention may include a Bischler-Napieralski cyclization reaction. In one embodiment, a Bischler-Napieralski cyclization reaction mixture comprising a β,γ-bicyclic ketone compound, a proton donor, and a proton donor anhydride is formed. In another embodiment, a Bischler-Napieralski cyclization reaction mixture may comprise a β,γ-bicyclic ketone compound and a proton donor anhydride, with the proton donor being an optional ingredient. Accordingly, it has now surprisingly been discovered that a Bischler-Napieralski cyclization may be effected by contacting β,γ-bicyclic ketone compound with a particular ratio of a proton donor and a proton donor anhydride. Without being bound by theory, contacting a β,γ-hexahydroisoquinolinone with a particular ratio of proton donor and proton donor anhydride may result in a Bischler-Napieralski cyclization that favors the formation of certain berberine compounds over other berberine compounds. Importantly, contacting a β,γ-hexahydroisoquinolinone with a particular ratio of proton donor and proton donor anhydride may produce a berberine compound comprising Formula (II), as defined above. In yet another aspect of the present invention, contacting a β,γ-hexahydroisoquinolinone with a particular ratio of proton donor and proton donor anhydride may produce a berberine compound comprising Formula (II) in greater yield than by-products such as nordihydrothebainone or α,β-bicyclic ketones.

(a) Reaction Schemes

For purposes of illustration, Reaction Scheme 1 depicts a process for the preparation of a berberine compound comprising Formula (II) in accordance with the present invention:

Reaction Scheme 1

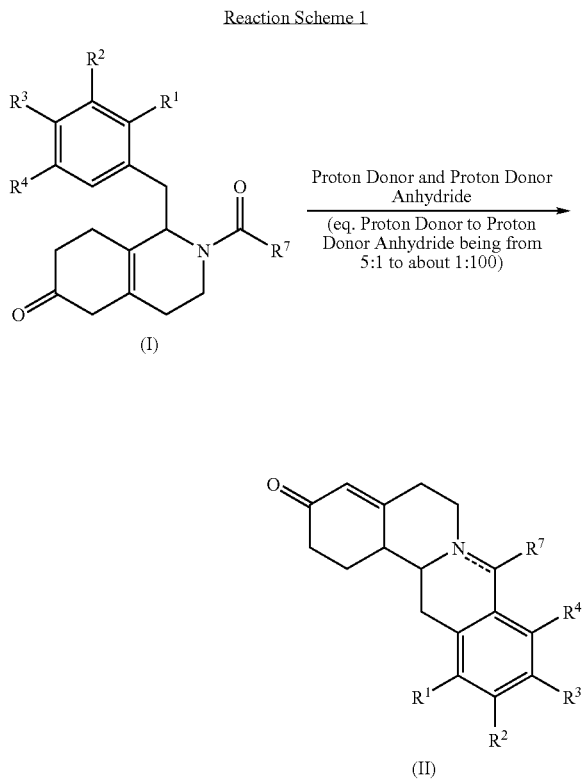

(I)

(II)

wherein:
- $R^1$, $R^2$, $R^3$, and $R^4$ are independently selected from the group consisting of cyano, hydroxyl, amino, hydrogen, halogen, hydrocarbyl, substituted hydrocarbyl, and ORS;
- $R^5$ is selected from the group consisting of hydrocarbyl and substituted hydrocarbyl; and
- $R^7$ is selected from the group consisting of hydrogen, hydrocarbyl, and substituted hydrocarbyl.

In another embodiment, Reaction Scheme 2 depicts a process for the preparation of a berberine compound comprising Formula (IIa) in accordance with the present invention:

Reaction Scheme 2

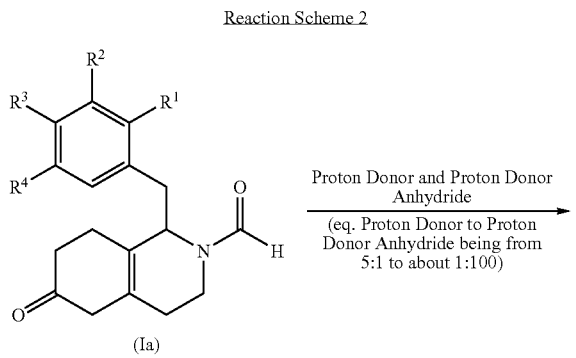

(Ia)

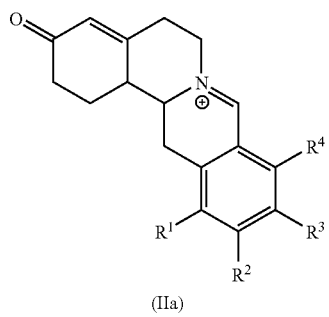

(IIa)

wherein: $R^1$, $R^2$, $R^3$, $R^4$, and $R^5$ are as defined above for Reaction Scheme 1. In a preferred embodiment of Reaction Scheme 2, the β,γ-bicyclic ketone starting material comprises the structure of Formula (Ib),

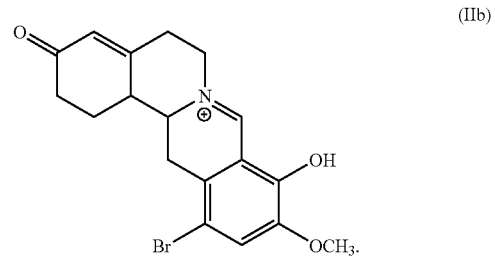

(Ib)

and the berberine product comprises the structure of Formula (IIb),

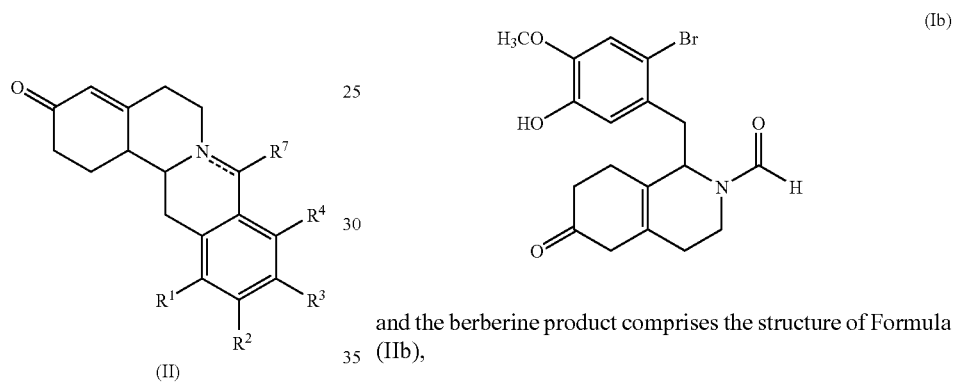

(IIb)

More specifically, Reaction Scheme 2 of the present invention may particularly include the following iteration, wherein the reaction mixture comprises 2.0 to 10.0 equivalents of trifluoromethanesulfonic anhydride per 1.0 equivalent of triflouoromethansulfonic acid.

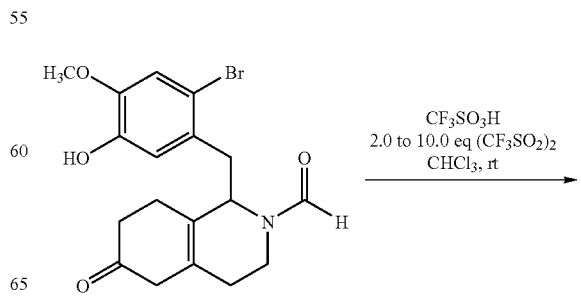

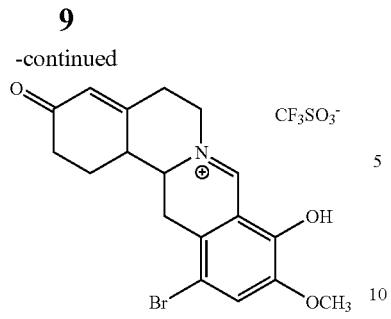

In yet another embodiment, Reaction Scheme 3 depicts a process for the preparation of a berberine compound comprising Formula (II) in accordance with the present invention:

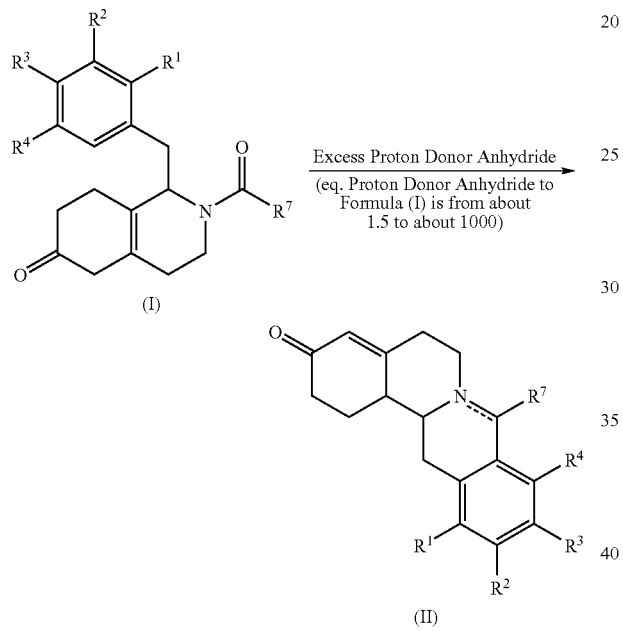

wherein: $R^1$, $R^2$, $R^3$, $R^4$, $R^5$ and $R^7$ are as defined above for Reaction Scheme 1.

In yet a further embodiment, Reaction Scheme 4 depicts a process for the preparation of a berberine compound comprising Formula (IIa) in accordance with the present invention:

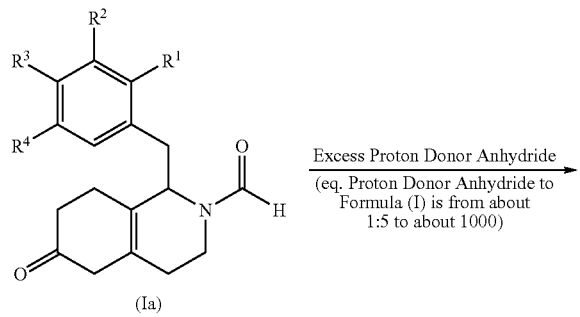

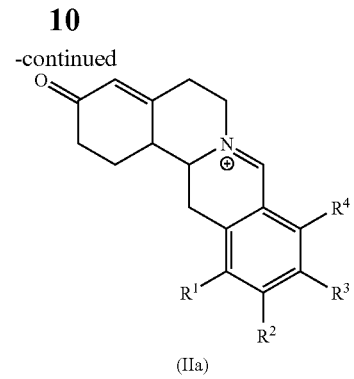

wherein: $R^1$, $R^2$, $R^3$, $R^4$, and $R^5$ are as defined above for Reaction Scheme 3.

(b) Bischler-Napieralski Reaction Mixture

In one embodiment, the process of the present invention generally comprises forming a Bischler-Napieralski reaction mixture comprising a proton donor, proton donor anhydride, and a β,γ-bicyclic ketone compound having the structure of Formula (I):

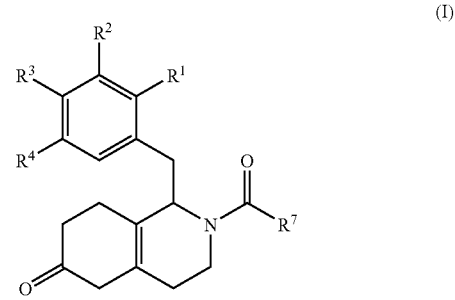

wherein:
  $R^1$, $R^2$, $R^3$, and $R^4$ are independently selected from the group consisting of cyano, hydroxyl, amino, hydrogen, halogen, hydrocarbyl, substituted hydrocarbyl, and OR5;
  $R^5$ is selected from the group consisting of hydrocarbyl and substituted hydrocarbyl; and
  $R^7$ is selected from the group consisting of hydrogen, hydrocarbyl, and substituted hydrocarbyl.

In one iteration for compounds comprising Formula (I), $R^1$, $R^2$, $R^3$, and $R^4$ are independently selected from the group consisting of hydrogen, halogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylether, haloalkoxy, haloalyl, heteroaryl, heterocyclic, hydroxyalkyl, and hydroxyl; and $R^7$ is selected from the group consisting of hydrogen, alkyl, and aryl. In an exemplary embodiment, $R^7$ is hydrogen.

In one alternative for compounds comprising Formula (I), the compound comprises Formula (Ia):

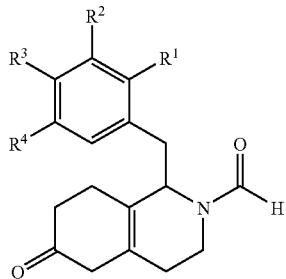

(Ia)

wherein: $R^1$, $R^2$, $R^3$, $R^4$, and $R^7$ are as defined for compounds comprising Formula (I).

In an exemplary embodiment, the compound comprising Formula (I) corresponds to a compound comprising Formula (Ib):

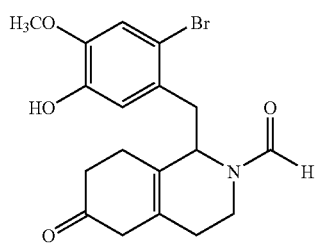

(Ib)

Other suitable β,γ-bicyclic ketone compounds corresponding to Formula (I) may include 1-(2-chloro-4,5-dihydroxybenzyl)-1,2,3,4,7,8-hexahydroisoquinolin-6(5H)-one, (R)-1-(2-chloro-4,5-dihydroxybenzyl)-1,2,3,4,7,8-hexahydroisoquinolin-6(5H)-one, (S)-1-(2-chloro-4,5-dihydroxybenzyl)-1,2,3,4,7,8-hexahydroisoquinolin-6(5H)-one, 1-(2-chloro-4,5-dihydroxybenzyl)-3,4,5,6,7,8-hexahydro-6-oxoisoquinoline-2(1H)carbaldehyde; (R)-1-(2-chloro-4,5-dihydroxybenzyl)-3,4,5,6,7,8-hexahydro-6-oxoisoquinoline-2(1H)carbaldehyde, (S)-1-(2-chloro-4,5-dihydroxybenzyl)-3,4,5,6,7,8-hexahydro-6-oxoisoquinoline-2(1H)carbaldehyde, 1-(2-bromo-4,5-dihydroxybenzyl)-1,2,3,4,7,8-hexahydroisoquinolin-6(5H)-one, (R)-1-(2-bromo-4,5-dihydroxybenzyl)-1,2,3,4,7,8-hexahydroisoquinolin-6(5H)-one, (S)-1-(2-bromo-4,5-dihydroxybenzyl)-1,2,3,4,7,8-hexahydroisoquinolin-6(5H)-one, 1-(2-bromo-4,5-dihydroxybenzyl)-3,4,5,6,7,8-hexahydro-6-oxoisoquinoline-2(1H)carbaldehyde, (R)-1-(2-bromo-4,5-dihydroxybenzyl)-3,4,5,6,7,8-hexahydro-6-oxoisoquinoline-2(1H)carbaldehyde, and (S)-1-(2-bromo-4,5-dihydroxybenzyl)-3,4,5,6,7,8-hexahydro-6-oxoisoquinoline-2(1H)carbaldehyde.

Among other factors affecting the Bischler-Napieralski cyclization reaction's ability to form a compound comprising Formula (II) is the ratio of proton donor to proton donor anhydride within the reaction medium or the total amount of proton donor anhydride without the presence of the proton donor. There is an optimum proton donor to proton donor anhydride range that causes the Bischler-Napieralski cyclization to occur, and to occur at a high yield, for compounds comprising Formula (II). Generally, the proton donor to proton donor anhydride ratio may be from 5:1 to about 1:100, more preferably from about 1:1 to about 1:20, and even more preferably from about 1:2 to about 1:10. The appropriate ratio of proton donor to proton donor anhydride may also minimize the rate of the isomerization of the β,γ-hexahydroisoquinolinone starting material into undesirable α,β-hexahydroisoquinolinones as well as the undesirable Grewe cyclization reaction product (i.e., nordihydrothebainone). The relative rates of the cyclization and isomerization reactions may be affected by the ratio of proton donor to proton donor anhydride, the solvent, the substrate, impurities and additives to the reaction mixture. As a non-limiting example, in one embodiment, the proton donor and proton donor anhydride are combined before being used in the Bischler-Napieralski cyclization of the β,γ-bicyclic ketone compound in order to reduce the formation of the α,β-ketone by-product and other undesired side reactions.

In one embodiment, the proton donor may comprise a strong acid, super acid or combinations thereof. In a preferred embodiment, the proton donor may provide a mixture having sufficient acidity to produce the Bischler-Napieralski cyclization. Suitable strong acids are those that are completely ionized in solution, usually water in the case of protic acids. Exemplary strong acids may be selected from the group consisting of benzenesulfonic acid, hydrochloric acid, hydrobromic acid, hydroiodic acid, methanesulfonic acid, nitric acid, phosphoric acid, polyphosphoric acid, sulfuric acid, trichloroacetic acid, trifluoroacetic acid, p-toluenesulfonic acid and combinations thereof. A preferred proton donor may comprise methanesulfonic acid or sulfuric acid. In one embodiment of the present invention, the proton donor may be selected from the group consisting of benzenesulfonic acid, hydrochloric acid, hydrobromic acid, hydroiodic acid, methanesulfonic acid, nitric acid, phosphoric acid, polyphoshoric acid, sulfuric acid, trichloroacetic acid, trifluoroacetic acid, p-toluenesulfonic acid, anhydrous hydrogen fluoride, fluorosulfonic acid, perchloric acid, perfluoroalkysulfonic acid, and combinations thereof; and the proton donor anhydride may be an anhydride of a proton donor selected from the group consisting of benzenesulfonic acid, hydrochloric acid, hydrobromic acid, hydroiodic acid, methanesulfonic acid, nitric acid, phosphoric acid, polyphoshoric acid, sulfuric acid, trichloroacetic acid, trifluoroacetic acid, p-toluenesulfonic acid, anhydrous hydrogen fluoride, fluorosulfonic acid, perchloric acid, perfluoroalkysulfonic acid, and combinations thereof.

It may be preferred to employ a super acid as the proton donor, along with the corresponding proton donor anhydride, in order to obtain the desired degree and rate of Bischler-Napieralski cyclization of the β,γ-bicyclic ketone compound. Super acids include all protic acids that are stronger than 100% sulfuric acid. Suitable super acids may include, but are not limited to, anhydrous hydrogen fluoride, fluorosulfonic acid, perchloric acid, perfluoroalkylsulfonic acids (e.g., perfluoro-1-octanesulfonic acid and trifluoromethanesulfonic acid) and combinations thereof or combinations with one or more Lewis acids such as antimony pentafluoride, boron trifluoride, phosphorous pentafluoride, and tantalum (V) fluoride. Some combinations of strong acids with super acids may also provide a mixture of sufficient acidity to produce the preferred degree of Bischler-Napieralski cyclization, including, for example, sulfuric or polyphosphoric acid combined with trifluoromethanesulfonic acid and/or fluorosulfonic acid.

The proton donor concentration in the Bischler-Napieralski cyclization reaction mixture varies depending on the identity of the acid used. For example, the acid concentration range may be from about 0.01 equivalents to about 10 equivalents; preferably, from about 0.01 equivalents to about 1.0 equivalents based on the concentration of the β,γ-bicyclic ketone starting material and the concentration of the proton donor anhydride. As noted previously, the proton donor to proton donor anhydride ratio may be from 5:1 to about 1:100, more preferably from about 1:1 to about 1:20, and even more preferably from about 1:2 to about 1:10.

The acid anhydrides used may comprise any anhydride of the strong and super acids noted above. For example, the acid anhydride may be selected from the group consisting of methanesulfonic anhydride, sulfur trioxide, or solutions in sulfuric acid (i.e., fuming sulfuric acid or oleums), phosphorous pentoxide or mixtures of phosphorous pentoxide in phosphoric acid (i.e., polyphosphoric acid), trifluoroacetic anhydride, trifluoromethanesulfonic anhydride, and combinations thereof. When a gaseous anhydride is used (e.g., $SO_3$), fuming sulfuric acid is added to the reaction medium. In accordance with one preferred embodiment, the acid anhydride corresponds to the strong acid or super acid used as the proton donor. In accordance with a preferred embodiment, the cyclizing proton donor and the proton donor anhydride are trifluoromethanesulfonic acid and trifluoromethanesulfonic anhydride, respectively.

Alternatively, the present invention may also comprise contacting a β,γ-hexahydroisoquinolinone starting material with an excess amount of proton donor anhydride to form a berberine compound without the presence of a proton donor. More specifically, the present invention may comprise contacting a compound comprising Formula (I) with a proton donor anhydride to form a berberine compound comprising Formula (II). For example, the present invention is also directed to a process for preparing a compound, the process comprising contacting a compound comprising Formula (I) with a proton donor anhydride, wherein the equivalents of proton donor anhydride to the compound comprising Formula (I) is from about 1.5 to about 1000, to form a compound comprising Formula (II) as defined above.

In either iteration of the invention (i.e., with or without proton donor), the Bischler-Napieralski cyclization of β,γ-bicyclic ketones is suitably carried out in an organic solvent. Typically, the β,γ-bicyclic ketone starting material is combined with the organic solvent prior to contacting with either the proton donor and proton donor anhydride to form the Bischler-Napieralski cyclization reaction mixture. In certain iterations, the β,γ-bicyclic ketone compound may be heated (e.g., at a temperature less than about 60° C.) under vacuum for several days to reduce the concentration of water present before being combined with the organic solvent (or other reactants). Suitable organic solvents may be selected from the group consisting of chloroform, dichloromethane, methyl sulfone, tetramethylene sulfone and combinations thereof. Preferably, the organic solvent comprises chloroform.

The Bischler-Napieralski cyclization may be conducted under inert atmosphere (e.g., argon or nitrogen gas) and the reaction mixture cooled and maintained at a reduced temperature during introduction of the proton donor and proton donor anhydride, since higher reaction temperatures tend to lead to more by-products and less of the desired berberine product. In one embodiment, the temperature of the Bischler-Napieralski cyclization mixture is maintained below about 15° C., more preferably, from about −10° C. to about 15° C., and even more preferably from about −5° C. to about 5° C. as the proton donor, proton donor anhydride, and the solution of β,γ-bicyclic ketone are being combined.

At the conclusion of the Bischler-Napieralski cyclization reaction, the reaction mixture may be quenched. For example, the Grewe reaction mixture may be quenched by the adding of a cooled (e.g., from about −10° C. to about 10° C.) aqueous solvent to the reaction mixture. The compound comprising Formula (II) may be readily recovered and isolated from the quenched Bischler-Napieralski reaction mixture using techniques known in the art. For example, a compound comprising Formula (II) may be extracted from the reaction mixture using an aqueous solvent (e.g., distilled water). Preferably, the quenched Bischler-Napieralski cyclization reaction may be extracted multiple times using an aqueous solvent to maximize the recovery of the comprising Formula (II) obtained.

Typically, the yield of the compound comprising Formula (II) may range from about 65% to about 95% by weight of the products formed. In one embodiment, the yield of the compound comprising Formula (II) may range from about 70% to about 80% by weight of the products formed. In another embodiment, the yield of the compound comprising Formula (II) may range from about 80% to about 90% by weight of the products formed. In a further embodiment, the yield of the compound comprising Formula (II) may be greater than 90% by weight of the products formed.

Definitions

The compounds described herein may have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denotes optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are simply intended to further illustrate and explain the present invention. The invention, therefore, should not be limited to any of the details in these examples.

Example 1

Bischler-Napieralski Cyclization Process for Preparing a Berberine Compound, with a 5:1 Proton Donor to Proton Donor Anhydride Ratio A mixture of 87.3 mL of trifluoromethane sulfonic acid (148.4 g, 1.0 moles) and 33.2 mL trifluoromethanesulfonic anhydride (55.81 g, 0.2 moles) was added to a 500 mL 3-neck round bottom flask. The mixture was heated to reflux under nitrogen. The solution was cooled to between 5° C. to 10° C. A solution of 38.99 g (0.10 moles) of 1-(2'-bromo-4'-methoxy-5'-hydroxybenzyl)-2-formyl-1,3,4,5,7,8-hexahydroisoquinolin-6-one (e.g., β,γ-hexahydroisoquinolinone) was dissolved in 250 mL of chloroform (anhydrous, amylene stabilized). The β,γ-hexahydroisoquinolinone chloroform solution was added dropwise to the trifluoromethanesulfonic acid solution at a constant rate over a period of 30 minutes and constantly stirred. The solution in the 3-neck round bottom flask was surrounded by an ice bath in order to keep the temperature of the solution under 15° C. during the addition of the β,γ-hexahydroisoquinolinone. After the combination of the solutions was complete, the reaction was allowed to warm to room temperature and stirred for about 19 hours. HPLC indicated none of the β,γ-hexahydroisoquinolinone was present. The mixture was then transferred by cannula (Teflon) into a mechanically stirred solution of 250 mL of water and ice. Following the stirring at room temperature for 45 minutes, the mixture was poured into a separatory funnel. The aqueous layer was washed with chloroform (3×100 mL). The aqueous layers were then combined and maintained at room temperature. After 7 days, a yellow crystalline compound formed. The crystals were isolated by filtration, and then dried on the funnel yielding 8.14 g of a berberine compound of the following formula:

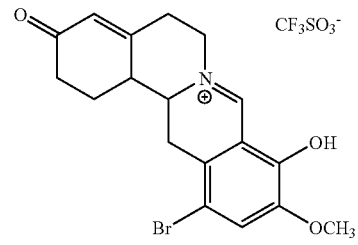

The identity of the berberine compound was then confirmed by mass spectroscopy, NMR spectroscopy (Bruker Avance 500 MHz), and HPLC.

Example 2

Bischler-Napieralski Cyclization Process for Preparing a Berberine Compound, with a 1:1 Proton Donor to Proton Donor Anhydride Ratio A mixture of 22.4 mL of trifluoromethane sulfonic acid (38.15 g, 0.25 moles) and 42.5 mL trifluoromethanesulfonic anhydride (71.47 g, 0.25 moles) was added to a 500 mL 3-neck round bottom flask. The mixture was heated to reflux under nitrogen. The solution was cooled to between 5° C. to 10° C. A solution of 19.95 g (0.05 moles) of 1-(2'-bromo-4'-methoxy-5'-hydroxybenzyl)-2-formyl-1,3,4,5,7,8-hexahydroisoquinolin-6-one (e.g., β,γ-hexahydroisoquinolinone) was dissolved in 50 mL of chloroform (anhydrous, amylene stabilized). The β,γ-hexahydroisoquinolinone chloroform solution was added dropwise to the trifluoromethanesulfonic acid solution at a constant rate over a period of 30 minutes and constantly stirred. The solution in the 3-neck round bottom flask was surrounded by an ice bath in order to keep the temperature of the solution under 15° C. during the addition of the β,γ-hexahydroisoquinolinone. After the combination of the solutions was complete, the reaction was allowed to warm to room temperature and stirred for about 72 hours. HPLC indicated that no β,γ-hexahydroisoquinolinone was present. The mixture was then transferred by cannula (Teflon) into a mechanically stirred solution of 200 g water and ice (100 g ice and 100 g water). Following the stirring at room temperature for 30 minutes, the mixture was poured into a separatory funnel. The chloroform extract was removed, and then the aqueous solution was extracted with 100 mL of $CHCl_3$. The chloroform layer was washed with distilled water (3×100 mL). The aqueous layers were then combined and maintained at room temperature. After 7 days, a yellow crystalline compound formed. The crystals were isolated by filtration, and then dried on the funnel yielding 7.9 g of a berberine compound of the following formula:

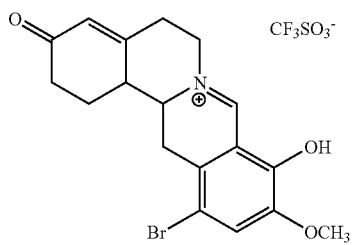

The identity of the berberine compound was then confirmed by mass spectroscopy, NMR spectroscopy (Bruker Avance 500 MHz), and HPLC.

The present invention is not limited to the above embodiments and may be variously modified. The above description of preferred embodiments is intended only to acquaint others skilled in the art with the invention, its principles and its practical application so that others skilled in the art may adapt and apply the invention in its numerous forms, as may be best suited to the requirements of a particular use.

What is claimed is:

1. A compound of Formula (II):

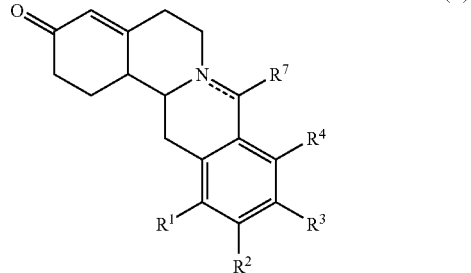

wherein:
$R^1$, $R^2$, $R^3$, and $R^4$ are independently selected from the group consisting of cyano, hydroxyl, amino, hydrogen, halogen, hydrocarbyl, substituted hydrocarbyl, and $OR^5$;
$R^5$ is selected from the group consisting of hydrocarbyl and substituted hydrocarbyl; and
$R^7$ is selected from the group consisting of hydrogen, hydrocarbyl, and substituted hydrocarbyl.

2. The compound of claim 1, wherein the compound comprises a counter-ion selected from the group consisting of chloride, bromide, iodide, trifluoroacetate, trifluoromethanesulfonate, methanesulfonate, acetate, p-toluenesulfonate, sulfate, bisulfate, phosphate, hydrogenphosphate, dihydrogenphosphate, fumarate, malonate, oxalate, formate, tartrate, benzoate, and a combination thereof.

3. The compound of claim 1, wherein:
$R^1$, $R^2$, $R^3$, and $R^4$ are independently selected from the group consisting of hydrogen, halogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylether, haloalkoxy, haloalyl, heteroaryl, heterocyclic, hydroxyalkyl, and hydroxyl; and
$R^7$ is selected from the group consisting of hydrogen, alkyl, and aryl.

4. The compound of claim 1, wherein: $R^1$ is halogen; $R^2$ is hydrogen; $R^3$ is $OR^5$; $R^4$ is hydroxyl; and $R^7$ is hydrogen.

5. A compound of Formula (IIa):

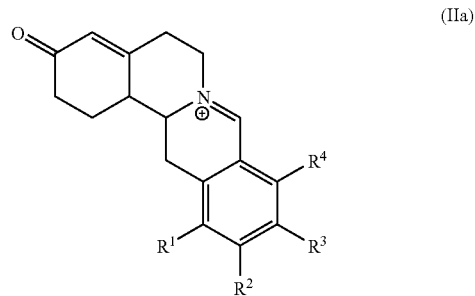

wherein:
$R^1$, $R^2$, $R^3$, and $R^4$ are independently selected from the group consisting of cyano, hydroxyl, amino, hydrogen, halogen, hydrocarbyl, substituted hydrocarbyl, and $OR^5$; and
$R^5$ is selected from the group consisting of hydrocarbyl and substituted hydrocarbyl.

6. The compound of claim 5, wherein the compound comprises a counter-ion selected from the group consisting of chloride, bromide, iodide, trifluoroacetate, trifluoromethanesulfonate, methanesulfonate, acetate, p-toluenesulfonate, sulfate, bisulfate, phosphate, hydrogenphosphate, dihydrogenphosphate, fumarate, malonate, oxalate, formate, tartrate, benzoate, and a combination thereof.

7. The compound of claim 5, wherein: $R^1$, $R^2$, $R^3$, and $R^4$ are independently selected from the group consisting of hydrogen, halogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylether, haloalkoxy, haloalyl, heteroaryl, heterocyclic, hydroxyalkyl, and hydroxyl.

8. The compound of claim 5, wherein: $R^1$ is halogen; $R^2$ is hydrogen; $R^3$ is $OCH_3$; and $R^4$ is hydroxyl.

9. A process for preparing a compound, the process comprising contacting a compound of Formula (I) with a proton donor and a proton donor anhydride, the molar ratio of proton donor to proton donor anhydride being from 5:1 to about 1:100, to form a compound of Formula (II) according to the following reaction scheme:

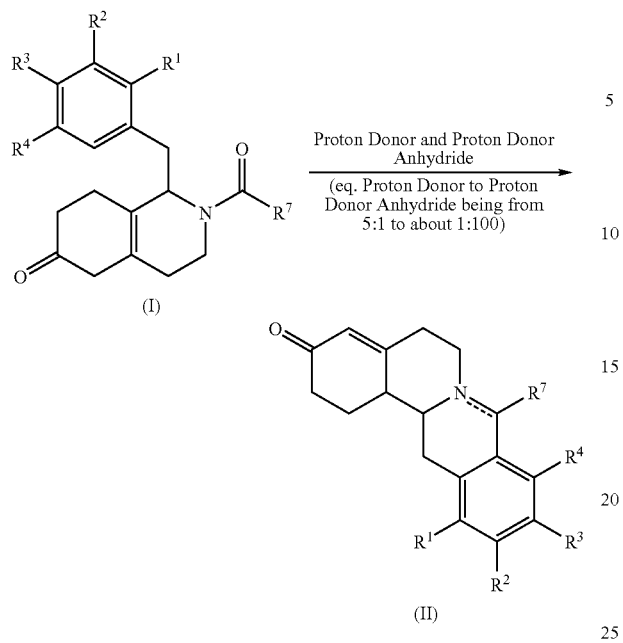

(I)

(II)

wherein:
R$^1$, R$^2$, R$^3$, and R$^4$ are independently selected from the group consisting of cyano, hydroxyl, amino, hydrogen, halogen, hydrocarbyl, substituted hydrocarbyl, and OR$^5$;
R$^5$ is selected from the group consisting of hydrocarbyl and substituted hydrocarbyl; and
R$^7$ is selected from the group consisting of hydrogen, hydrocarbyl, and substituted hydrocarbyl.

10. The process of claim 9, wherein the molar ratio of proton donor to proton donor anhydride is from about 1:1 to about 1:20; the reaction is conducted at a temperature below about 15° C.;
R$^1$, R$^2$, R$^3$, and R$^4$ are independently selected from the group consisting of hydrogen, halogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylether, haloalkoxy, haloalyl, heteroaryl, heterocyclic, hydroxyalkyl, and hydroxyl;
R$^7$ is selected from the group consisting of hydrogen, alkyl, and aryl; and
the proton donor is selected from the group consisting of benzenesulfonic acid, hydrochloric acid, hydrobromic acid, hydroiodic acid, methanesulfonic acid, nitric acid, phosphoric acid, polyphoshoric acid, sulfuric acid, trichloroacetic acid, trifluoroacetic acid, p-toluenesulfonic acid, anhydrous hydrogen fluoride, fluorosulfonic acid, perchloric acid, perfluoroalkysulfonic acid, and combinations thereof; and the proton donor anhydride is an anhydride of a proton donor selected from the group consisting of benzenesulfonic acid, hydrochloric acid, hydrobromic acid, hydroiodic acid, methanesulfonic acid, nitric acid, phosphoric acid, polyphoshoric acid, sulfuric acid, trichloroacetic acid, trifluoroacetic acid, p-toluenesulfonic acid, anhydrous hydrogen fluoride, fluorosulfonic acid, perchloric acid, perfluoroalkysulfonic acid, and combinations thereof.

11. The process of claim 9, wherein the yield of the compound of Formula (II) is at least 80% by weight of the products formed.

12. The process of claim 9, wherein the compound of Formula (I) of a compound corresponding to Formula (Ia):

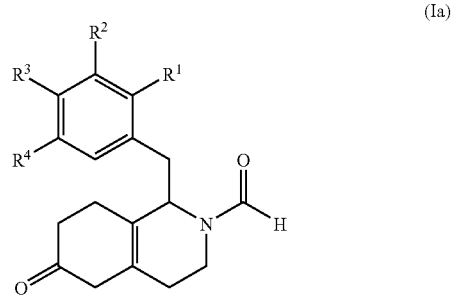

(Ia)

and the compound of Formula (II) is a compound corresponding to Formula (IIa):

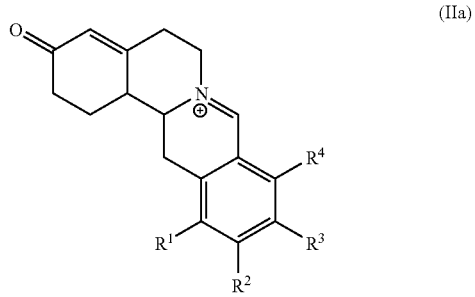

(IIa)

wherein:
R$^1$, R$^2$, R$^3$, and R$^4$ are as defined in claim 9.

13. The process of claim 12, wherein the molar ratio of proton donor to proton donor anhydride is from about 1:2 to about 1:10; the reaction is conducted at a temperature below about 15° C.; R$^1$, R$^2$, R$^3$, and R$^4$ are independently selected from the group consisting of hydrogen, halogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylether, haloalkoxy, haloalyl, heteroaryl, heterocyclic, hydroxyalkyl, and hydroxyl; and the proton donor is selected from the group consisting of benzenesulfonic acid, hydrochloric acid, hydrobromic acid, hydroiodic acid, methanesulfonic acid, nitric acid, phosphoric acid, polyphoshoric acid, sulfuric acid, trichloroacetic acid, trifluoroacetic acid, p-toluenesulfonic acid, anhydrous hydrogen fluoride, fluorosulfonic acid, perchloric acid, perfluoroalkysulfonic acid, and combinations thereof; and the proton donor anhydride is an anhydride of a proton donor selected from the group consisting of benzenesulfonic acid, hydrochloric acid, hydrobromic acid, hydroiodic acid, methanesulfonic acid, nitric acid, phosphoric acid, polyphoshoric acid, sulfuric acid, trichloroacetic acid, trifluoroacetic acid, p-toluenesulfonic acid, anhydrous hydrogen fluoride, fluorosulfonic acid, perchloric acid, perfluoroalkysulfonic acid, and combinations thereof.

14. The process of claim 9, wherein the compound of Formula (I) is a compound corresponding to Formula (Ib):

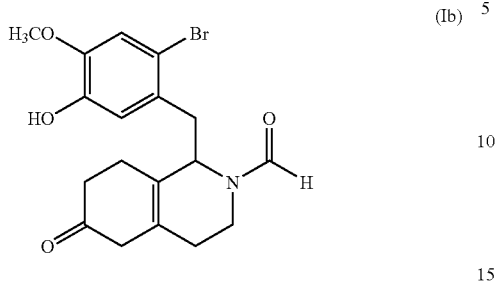

and the compound of Formula (II) is a compound corresponding to Formula (IIb):

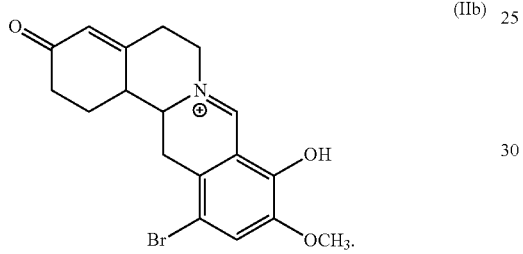

15. The process of claim 14, wherein the proton donor is trifluoromethanesulfonic acid and the proton donor anhydride is trifluoromethanesulfonic anhydride.

16. The process of claim 15, wherein the ratio of trifluoromethanesulfonic acid to trifluoromethanesulfonic anhydride is from about 1:2 to about 1:10.

17. A process for preparing a compound, the process of contacting a compound of Formula (I) with a proton donor anhydride, wherein the equivalents of proton donor anhydride to the compound of Formula (I) is from about 1.5 to about 1000, to form a compound of Formula (II) according to the following reaction scheme:

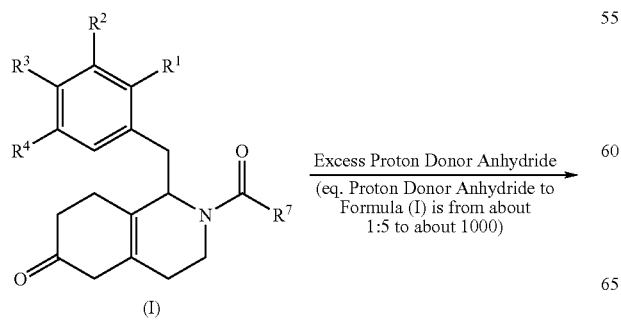

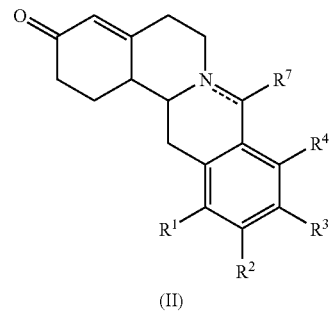

wherein:

$R^1$, $R^2$, $R^3$, and $R^4$ are independently selected from the group consisting of cyano, hydroxyl, amino, hydrogen, halogen, hydrocarbyl, substituted hydrocarbyl, and $OR^5$;

$R^5$ is selected from the group consisting of hydrocarbyl and substituted hydrocarbyl; and $R^7$ is selected from the group consisting of hydrogen, hydrocarbyl, and substituted hydrocarbyl.

18. The process of claim 17, wherein the reaction is conducted at a temperature below about 15° C.; the yield of the compound comprising Formula (II) is at least 65% by weight of the products formed;

$R^1$, $R^2$, $R^3$, and $R^4$ are independently selected from the group consisting of hydrogen, halogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylether, haloalkoxy, haloalyl, heteroaryl, heterocyclic, hydroxyalkyl, and hydroxyl; and $R^7$ is hydrogen, alkyl, or aryl.

19. The process of claim 17, wherein the compound of Formula (I) is a compound corresponding to Formula (Ia):

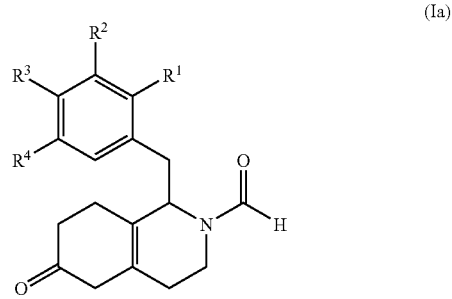

and the compound of Formula (II) is a compound corresponding to Formula (IIa):

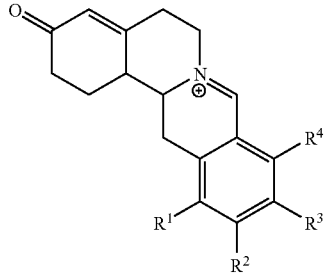

(IIa)

wherein:

R¹, R², R³, and R⁴ are as defined in claim 17.

20. The process of claim 19, wherein R¹, R², R³, and R⁴ are independently selected from the group consisting of hydrogen, halogen, substituted and unsubstituted acyl, alkenyl, alkoxy, alkoxyaryl, alkyl, alkylamino, alkylthio, alkynyl, amino, aryl, arylalkoxy, carboalkoxy, carboxyalkenyl, carboxyalkyl, carboxyl, cyano, cyanoalkyl, cycloalkyl, cycloalkylether, haloalkoxy, haloalyl, heteroaryl, heterocyclic, hydroxyalkyl, and hydroxyl.

21. The process of claim 17, wherein the compound of Formula (I) is a compound corresponding to Formula (Ib):

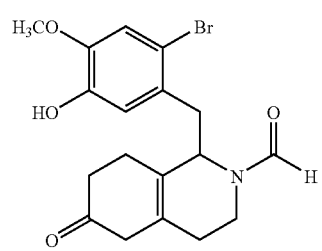

(Ib)

and the compound of Formula (II) is a compound corresponding to Formula (IIb):

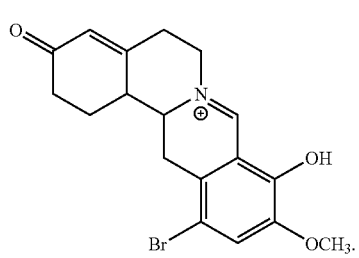

(IIb)

22. The process of claim 21, wherein the proton donor anhydride is trifluoromethanesulfonic anhydride.

* * * * *